(12) United States Patent
Hodgkinson et al.

(10) Patent No.: US 9,316,630 B2
(45) Date of Patent: Apr. 19, 2016

(54) ANTI-CLOG AND NON-METALLIC DEBRIS DETECTOR FOR LUBRICATION SYSTEM INLET

(71) Applicant: Sikorsky Aircraft Corporation, Stratford, CT (US)

(72) Inventors: Eric James Hodgkinson, New Hartford, CT (US); David M. Lutian, Milford, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 244 days.

(21) Appl. No.: 14/074,893

(22) Filed: Nov. 8, 2013

(65) Prior Publication Data

US 2015/0129361 A1    May 14, 2015

(51) Int. Cl.
| | |
|---|---|
| *F01M 11/10* | (2006.01) |
| *G01N 33/28* | (2006.01) |
| *B64C 27/00* | (2006.01) |
| *B64D 45/00* | (2006.01) |
| *F01M 1/10* | (2006.01) |
| *F16N 29/02* | (2006.01) |
| *F16N 29/04* | (2006.01) |

(52) U.S. Cl.
CPC ............ *G01N 33/2835* (2013.01); *B64C 27/00* (2013.01); *B64D 45/00* (2013.01); *F01M 1/10* (2013.01); *F01M 11/10* (2013.01); *F16N 29/02* (2013.01); *F16N 29/04* (2013.01); *G01N 33/2858* (2013.01); *G01N 33/2888* (2013.01); *F01M 2001/1042* (2013.01); *F01M 2011/1466* (2013.01); *Y10T 137/7837* (2015.04); *Y10T 137/8225* (2015.04)

(58) Field of Classification Search
CPC .......... G01N 33/2835; G01N 33/2858; G01N 33/2888; B64C 27/00; B64D 45/00; F01M 1/10; F01M 11/10; F01M 2011/1466; F01M 2001/1042; F16N 29/02; F16N 29/04
USPC .......................................................... 184/6.4
See application file for complete search history.

(56) References Cited

U.S. PATENT DOCUMENTS

| | | | |
|---|---|---|---|
| 1,742,758 A | 11/1924 | Curphey | |
| 2,548,160 A | 9/1945 | Hunter | |
| 3,323,649 A * | 6/1967 | Rosaen | ................ B01D 35/143 116/268 |

(Continued)

FOREIGN PATENT DOCUMENTS

| | | |
|---|---|---|
| EP | 0110410 A2 | 6/1984 |
| EP | 2014877 A2 | 1/2009 |
| GB | 2195263 A | 4/1988 |

OTHER PUBLICATIONS

European Search Report for application EP 141918554, dated Jun. 3, 2015, 7 pages.

*Primary Examiner* — William A Rivera
*Assistant Examiner* — Michael Riegelman
(74) *Attorney, Agent, or Firm* — Cantor Colburn LLP

(57) ABSTRACT

A contaminant detection system for use in a fluid distribution system includes a first detector assembly including an inlet housing and detector screen through which fluid in the fluid distribution system passes and a first sensor to detect a first type of contaminant caught in the detector screen; and a second detector assembly including a second sensor which activates when the inlet housing or detector screen is clogged to detect whether the fluid contains a second type of contaminant when the first sensor does not detect the first type of contaminant.

17 Claims, 3 Drawing Sheets

(56) References Cited

U.S. PATENT DOCUMENTS

| | | | |
|---|---|---|---|
| 3,817,380 A | 6/1974 | Brown | |
| 3,878,103 A * | 4/1975 | Miller | G01N 15/0618 174/117 M |
| 4,304,663 A | 12/1981 | Manders | |
| 4,512,298 A | 4/1985 | Hayashi | |
| 4,657,671 A * | 4/1987 | Botstiber | B01D 29/117 210/111 |
| 4,699,509 A * | 10/1987 | Kamiya | G01N 21/255 356/436 |
| 4,732,190 A * | 3/1988 | Polselli | F16K 17/24 137/460 |
| 4,735,286 A | 4/1988 | Miki et al. | |
| 4,756,824 A | 7/1988 | Howard, Jr. et al. | |
| 4,854,276 A | 8/1989 | Elsbett et al. | |
| 5,118,410 A * | 6/1992 | Rumberger | B01D 35/143 210/243 |
| 5,121,599 A * | 6/1992 | Snyder | F01D 25/20 184/6.11 |
| 5,239,861 A * | 8/1993 | Fujita | B01D 29/05 116/DIG. 42 |
| 5,610,341 A * | 3/1997 | Tortora | F01D 17/02 73/756 |
| 6,116,272 A * | 9/2000 | Kratzet | F01M 1/16 137/516.11 |
| 6,459,995 B1 * | 10/2002 | Collister | G01N 27/221 702/104 |
| 6,776,261 B2 * | 8/2004 | Eriksen | F16C 19/52 184/6.4 |
| 8,215,454 B2 | 7/2012 | Portlock | |
| 8,226,822 B2 | 7/2012 | Paradise | |
| 2006/0081419 A1 * | 4/2006 | Care | F01D 25/20 184/6.11 |
| 2006/0137939 A1 | 6/2006 | Smolong | |
| 2008/0116009 A1 * | 5/2008 | Sheridan | F01D 25/18 184/6.4 |
| 2009/0014245 A1 * | 1/2009 | Shevchenko | F01D 21/10 184/6.4 |
| 2011/0315112 A1 * | 12/2011 | Manta | F01M 1/10 123/196 A |
| 2013/0008745 A1 * | 1/2013 | Barrett | F02C 7/06 184/6.11 |

\* cited by examiner

ANTI-CLOG AND NON-METALLIC DEBRIS DETECTOR FOR LUBRICATION SYSTEM INLET

BACKGROUND

The subject matter disclosed herein relates generally to a lubricant distribution, and in particular to a lubricant distribution assembly for a rotary wing aircraft that provides detection of different types of contaminants in the lubricant.

Existing rotary wing aircraft employ a lubricant distribution assembly to convey lubricant to one or more gearboxes. An existing lubricant distribution assembly has a single inlet housing with a chip detector sensor and chip detector screen. The chip detector sensor and chip detector screen capture and detect metallic contaminants in the lubricant that is traveling to the lubricant pumps. A drawback to the existing lubricant distribution assembly is that excessive debris may clog the chip detector screen or inlet housing and prevent lubricant from passing through the inlet housing to the lubricant pumps.

SUMMARY

In one exemplary embodiment, a contaminant detection system for use in a fluid distribution system includes a first detector assembly including an inlet housing and detector screen through which fluid in the fluid distribution system passes and a first sensor to detect a first type of contaminant caught in the detector screen; and a second detector assembly including a second sensor which activates when the detector screen or inlet housing is clogged to detect whether the fluid contains a second type of contaminant when the first sensor does not detect the first type of contaminant.

In another exemplary embodiment, a fluid distribution assembly for distributing a fluid includes a first inlet housing; an outlet housing; a chip detector assembly including a chip detector screen through which the fluid passes between the first inlet and outlet housings, and a chip detector sensor which senses a first type of contaminant on the chip detector screen; a second inlet housing fluidly coupled to the outlet housing; a check valve in the second inlet housing which opens when the chip detector screen or first inlet housing is clogged to allow the fluid to pass between the second inlet housing and the outlet housing, and is closed when the first inlet housing or chip detector screen is not clogged to prevent the fluid to from passing between the second inlet housing and the outlet housing; a check valve sensor in communication with the check valve, the check valve sensor producing a signal indicative of when the check valve opens.

In another exemplary embodiment, a rotary wing aircraft includes a rotor, a gearbox coupled to the rotor; an engine coupled to the gearbox; a lubricant distribution system providing lubricant from a sump to the gearbox, the lubricant distribution system including: a first detector assembly including an inlet housing and detector screen through which fluid in the fluid distribution system passes and a first sensor to detect a first type of contaminant caught in the detector screen; and a second detector assembly including a second sensor which activates when the detector screen or inlet housing is clogged to detect whether the fluid contains a second type of contaminant when the first sensor does not detect the first type of contaminant.

Other aspects, features, and techniques of the invention will become more apparent from the following description taken in conjunction with the drawings.

BRIEF DESCRIPTION OF THE DRAWINGS

Referring now to the drawings wherein like elements are numbered alike in the several FIGURES, in which.

DETAILED DESCRIPTION

Figure 1:
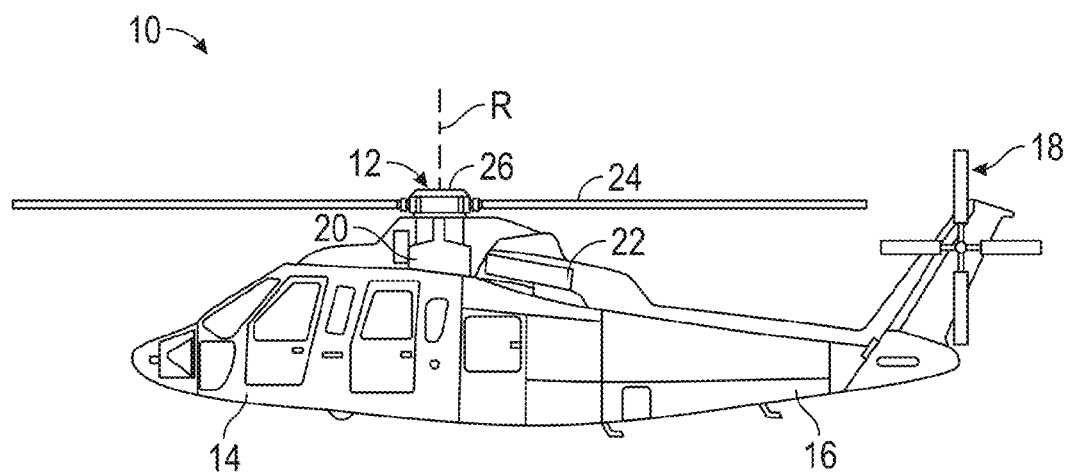
FIG. 1 illustrates a rotary wing aircraft in an exemplary embodiment.

FIG. 1 schematically illustrates a rotary-wing aircraft 10 having a main rotor assembly 12. The aircraft 10 includes an airframe 14 having an extending tail 16 which mounts a tail rotor system 18, such as an anti-torque system, a translational thrust system, a pusher propeller, a rotor propulsion system, and the like. The main rotor assembly 12 is driven about an axis of rotation R through a main gearbox 20 by one or more engines 22. The main rotor assembly 12 includes a multiple of rotor blades 24 mounted to a rotor hub 26. Although a particular helicopter configuration is illustrated and described in the disclosed embodiment, other configurations and/or machines, such as high speed compound rotary wing aircraft with supplemental translational thrust systems, dual contra-rotating, coaxial rotor system aircraft, turbo-props, tilt-rotors and tilt-wing aircraft, will also benefit from embodiments of the invention.

Figure 2:
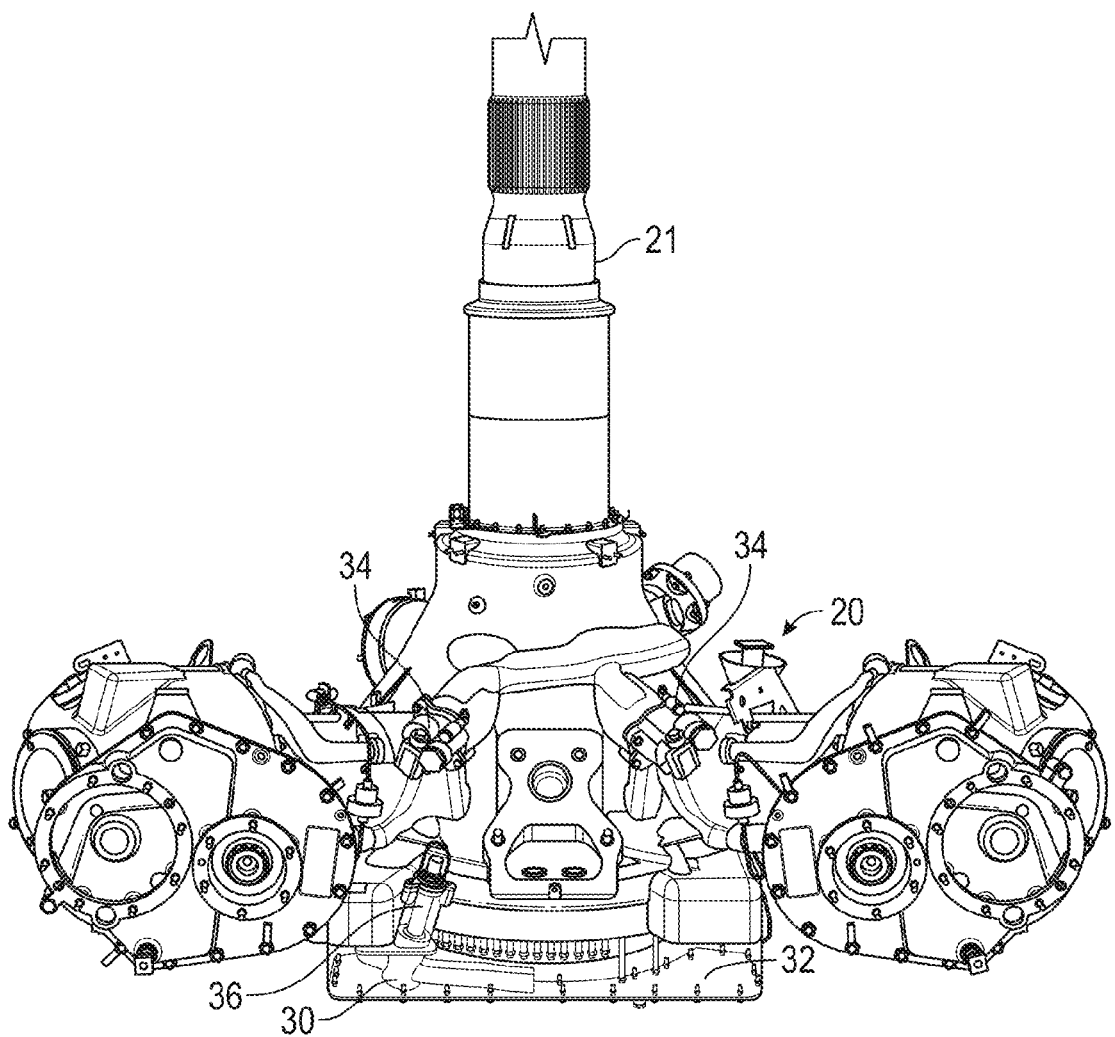
FIG. 2 depicts a gearbox and rotor shaft in an exemplary embodiment.

FIG. 2 depicts a gearbox assembly 20 and main rotor shaft 21 in an exemplary embodiment. A lubricant distribution assembly 30 is positioned in a lubricant sump 32. Lubricant pumps 34 draw lubricant (e.g., oil) from the sump 32, through the lubricant distribution assembly 30 and supply lubricant to gearbox assembly 20. A chip detector assembly 36 is mounted to the lubricant distribution assembly 30 as described in further detail herein. While described as a lubricant in the context of gearbox assembly 20, it is understood that, in other aspects, the lubricant is only one type of fluid usable with the invention. By way of example, the fluid could be fuel where the sump 32 is a gas tank and the lubricant distribution assembly 30 pumps fuel to an engine. By way of another example, the fluid could be coolant where the sump 32 is a coolant reservoir and the lubricant distribution assembly 30 pumps coolant to cool an engine. However, the invention is not limited thereto.

Figure 3:
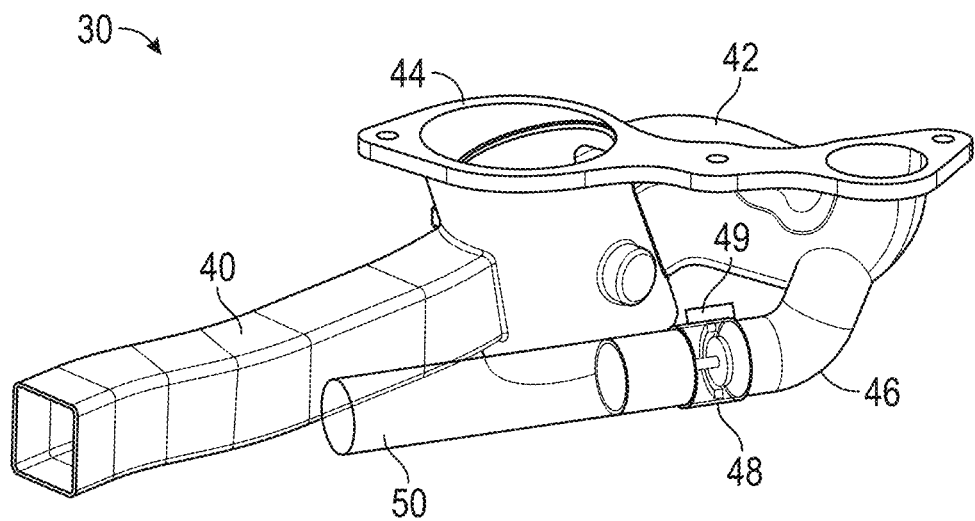
FIG. 3 depicts a lubricant distribution assembly in an exemplary embodiment.

FIG. 3 depicts a lubricant distribution assembly 30 in an exemplary embodiment. Lubricant distribution assembly 30 includes an inlet housing 40. Inlet housing 40 is a hollow member for placement in sump 32. Inlet housing 40 is in fluid communication with an outlet housing 42. An outlet of outlet housing 42 is in fluid communication with lubricant pump(s) 34. Interposed between inlet housing 40 and outlet housing 42 is a chip detector cavity 44 in fluid communication with inlet housing 40 and outlet housing 42. Chip detector cavity 44 is a generally cylindrical member, having a hollow interior to receive a portion of chip detector assembly 36.

Lubricant distribution assembly 30 also includes a second inlet housing 46 in fluid communication with outlet housing 42. Second inlet housing 46 is fluidly coupled to outlet housing 42 downstream of chip detector cavity 44. A check valve 48 (normally closed) is positioned at an inlet end of the second inlet housing 46. A check valve sensor 49 generates a signal when check valve 48 transitions from closed to open. Check valve sensor 49 may be a contact sensor that is activated by a portion of check valve 48. A generally cylindrical inlet screen 50 is positioned at an inlet to the check valve 48. Inlet screen 50 filters contaminants from the lubricant. Inlet screen 50 may be a large surface area screen to prevent clogging of secondary inlet and therefore maintain oil flow to critical bearings and gear meshes. Inlet screen 50, check valve 48 and second inlet housing 46 are also positioned in sump 32.

Figure 4:
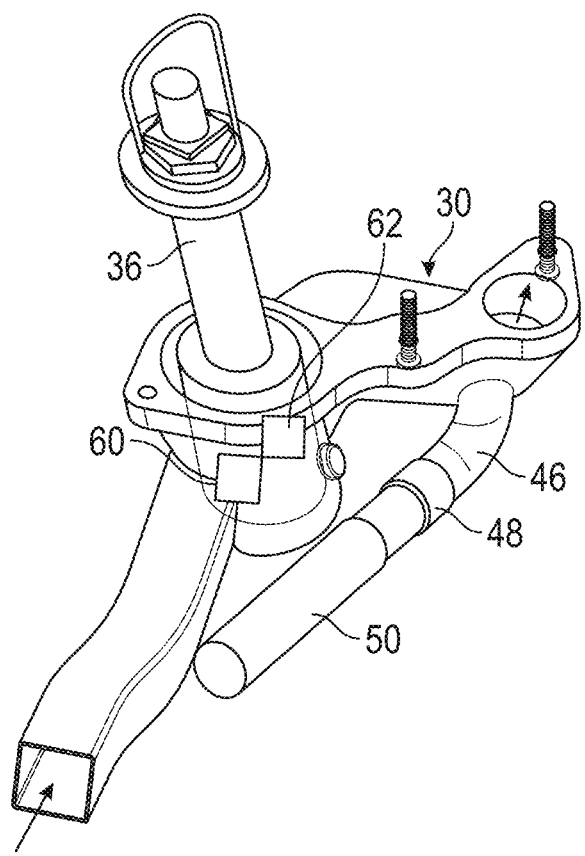
FIG. 4 depicts a lubricant distribution system in an exemplary embodiment.

FIG. 4 depicts a lubricant distribution system including chip detector assembly 36 mounted to the lubricant distribution assembly 30. Chip detector assembly 36 includes a chip detector screen 60 to capture contaminants in lubricant traveling from inlet housing 40 to outlet housing 42. Lubricant traveling from inlet housing 40 to outlet housing 42 passes through chip detector screen 60. Metal contaminants captured by the chip detector screen 60 are detected by a chip detector sensor 62. Chip detector sensor 62 may use one or more magnets to attract ferrous metals or use conductivity of non-ferrous metals to detect the presence of metal contaminants. Chip detector sensor 62 generates a signal when a sufficient amount of metal contaminants are present. This is an indication of a first type of contaminant in the form of metal chips.

In normal operation, check valve 48 is closed and lubricant flows from sump 32, to inlet housing 40, through chip detector screen 60, chip detector cavity 44 and outlet housing 42. In the event that metal contaminants are detected, chip detector sensor 62 generates a signal indicating the presence a first type of contaminant (e.g., metal contaminants). During operation, larger contaminants can accumulate on chip detector screen 60, impeding the flow of lubricant to outlet housing 42. Additionally, foreign object debris (FOD) may clog inlet housing 40. When the flow of lubricant through inlet housing 40 or chip detector screen 60 is reduced below some limit, check valve 48 opens in response to a pressure differential across check valve 48 caused by a reduced pressure in outlet housing 42 produced by lubricant pumps 34. When check valve 48 opens, check valve sensor 49 generates a signal indicating that the inlet housing 40 is blocked by a second contaminant (e.g., larger contaminants, either metallic or non-metallic). Lubricant from sump 32 travels through inlet screen 50, check valve 48, second inlet housing 46 and outlet housing 42.

Figure 5:
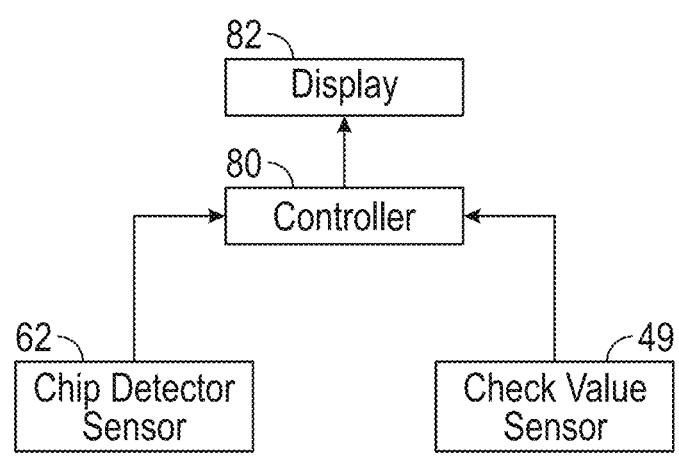
FIG. 5 depicts a control system in an exemplary embodiment.

FIG. 5 depicts a control system in an exemplary embodiment. Control system includes a controller 80 coupled to a display 82. Controller 80 may be implemented using a general purpose processor executing a computer program stored on a storage medium. Controller 80 may be a standalone device, or part of a more encompassing flight control system of aircraft 10. Display 82 may be positioned in the cockpit of aircraft 10, as an instrument panel indicator(s), a light, a panel display, heads up display, head mounted display, etc.

Controller 80 receives signals from chip detector sensor 62 and check valve sensor 49 and generates an indication on display 82. A first indication results when neither the chip detector sensor 62 nor check valve sensor 49 produces a signal. This indicates normal operation mode. A second indication results when the chip detector sensor 62 produces a signal but check valve sensor 49 does not produce a signal. This indicates the presence of a first type of contaminant (e.g., metal contaminants) in the lubricant. A third indication results when the chip detector sensor 62 does not produce a signal and check valve sensor 49 produces a signal. This indicates that inlet housing 40 or chip detector screen 60 has clogged, causing check valve 48 to open. This is an indication of a second type of contaminant (e.g., non-metallic) in the lubricant. A fourth indication results when the chip detector sensor 62 produces a signal and check valve sensor 49 produces a signal. This is an indication of both the first type of contaminant and the second type of contaminant in the lubricant (i.e., both metallic and non-metallic contaminants) or an extreme amount of the first type of contaminant sufficient to clog the inlet housing 40 or screen 60. While described in terms of the indication being visual on the display 82, it is understood that in other aspects the indication can be tactile or audible in addition to or instead of the visual indication on the display 82.

Embodiments use a second inlet housing to bypass a clogged inlet housing and prevent damage from occurring to system components. The use of a check valve sensor in the second inlet housing allows the pilot to be aware of a large contamination event that otherwise would not be detected by the chip detector assembly.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions, or equivalent arrangement not hereto described will be apparent to those of ordinary skill in the art without departing from the scope and spirit of the invention. By way of example, while described in terms of use on an aircraft, aspects can be used in automobiles, other types of aircrafts beyond rotorcraft, ships, industrial machinery, pipelines, septic or sewer systems, or any other system where fluid flow needs to be maintained and contaminant detection is important. Additionally, while various embodiment of the invention have been described, it is to be understood that aspects of the invention may include only some of the described embodiments. Accordingly, the invention is not to be seen as limited by the foregoing description, but is only limited by the scope of the appended claims.

What is claimed is:

1. A contaminant detection system for use in a fluid distribution system, the contaminant detection system comprising:
    a first detector assembly including an inlet housing and detector screen through which fluid in the fluid distribution system passes and a first sensor to detect a first type of contaminant caught in the detector screen; and
    a second detector assembly including a second sensor which activates when one of the inlet housing and the detector screen is clogged to detect whether the fluid contains a second type of contaminant that is distinct from the first type of contaminant when the first sensor does not detect the first type of contaminant.

2. The contaminant detection system of claim 1, wherein:
    the second detector assembly includes a check valve at an inlet through which the fluid does not pass when the inlet housing or detector screen is not clogged, and through which the fluid does pass when the inlet housing or detector screen is clogged, and
    the second sensor is in communication with the check valve, the second sensor producing a signal indicative of the state of the check valve.

3. The contaminant detection system of claim 1, further comprising:
    a controller coupled to the first and second sensors; and
    a display coupled to the controller;
    the controller generating an indication on the display in response to the first sensor and the second sensor to selectively indicate and differentiate between the first and second types of contaminant in the fluid.

4. The lubricant distribution system of claim 3 wherein:
the controller generates a first indication when neither the first sensor nor the second sensor produces a signal;
the controller generates a second indication when the first sensor produces a signal and the second sensor does not produce a signal to indicate a presence of the first type of contaminant in the fluid;
the controller generates a third indication when the first sensor does not produce a signal and the second sensor produces a signal to indicate a presence of the second type of contaminant in the fluid, the second type of contaminant being other than the first type and not being detectable by the first detector; and
the controller generates a fourth indication when each of the first and second sensors produce a signal to indicate a presence of one of the first type of contaminant in the lubricant and the presence of the second type of contaminant in the lubricant in sufficient quantity to clog the one of the inlet housing and the detector screen.

5. The contaminant detection system of claim 1, wherein the first type is a metal contaminant and the second type is a non-metal contaminant.

6. The contaminant detection system of claim 1, wherein the second type of contaminant is not detectable by the first sensor.

7. A fluid distribution assembly for distributing a fluid, the assembly comprising:
a first inlet housing;
an outlet housing;
a chip detector assembly including a chip detector screen through which the fluid passes between the first inlet and outlet housings, and a chip detector sensor which senses a first type of contaminant on the chip detector screen;
a second inlet housing fluidly coupled to the outlet housing;
a check valve in the second inlet housing which opens when the first inlet housing or chip detector screen is clogged to allow the fluid to pass between the second inlet housing and the outlet housing, and is closed when the first inlet housing or chip detector screen is not clogged to prevent the fluid to from passing between the second inlet housing and the outlet housing; and
a check valve sensor in communication with the check valve, the check valve sensor producing a signal indicative of when the check valve opens.

8. The fluid distribution assembly of claim 7 further comprising:
an inlet screen positioned at an inlet of the second inlet housing, the inlet screen to filter first and other types of contaminants from the fluid when the check valve is open.

9. The fluid distribution assembly of claim 7 further comprising:
a controller coupled to the chip detector sensor and the check valve sensor; and
a display coupled to the controller;
the controller generating an indication on the display in response to the chip detector sensor and the check valve sensor to selectively indicate and differentiate between the first and other types of contaminant in the fluid.

10. The fluid distribution assembly of claim 9, wherein:
the controller generates a first indication when neither the chip detector sensor nor the check valve sensor produces a signal;
the controller generates a second indication when the chip detector sensor produces a signal and the check valve sensor does not produce a signal to indicate a presence of the first type of contaminant in the fluid;
the controller generates a third indication when the chip detector sensor does not produce a signal and the check valve sensor produces a signal to indicate a presence of the second type of contaminant in the fluid, the second type of contaminant being other than the first type and not being detectable by the chip detector; and
the controller generates a fourth indication when the chip detector and check valve sensors both produce a signal to indicate a presence of the first type of contaminant in the lubricant and/or the presence of the second type of contaminant in the lubricant and in sufficient quantity to clog the first inlet housing or the chip detector screen.

11. The fluid distribution assembly of claim 10, wherein the first type is a metal contaminant and the second type is a non-metal contaminant.

12. A rotary wing aircraft comprising:
a rotor;
a gearbox coupled to the rotor;
an engine coupled to the gearbox;
a lubricant distribution system providing lubricant from a sump to the gearbox, the lubricant distribution system including:
a first detector assembly including an inlet housing and a detector screen through which fluid in the fluid distribution system passes and a first sensor to detect a first type of contaminant caught in the detector screen;
a second detector assembly including a second sensor which activates when one of the inlet housing and the detector screen is clogged to detect whether the fluid contains a second type of contaminant that is distinct from the first type contaminant when the first sensor does not detect the first type of contaminant.

13. The rotary wing aircraft of claim 12, wherein:
the second detector assembly includes a check valve at an inlet through which the fluid does not pass when the inlet housing or detector screen is not clogged, and through which the fluid does pass when the inlet housing or detector screen is clogged, and
the second sensor is in communication with the check valve, the second sensor producing a signal indicative of the state of the check valve.

14. The rotary wing aircraft of claim 12, further comprising:
a controller coupled to the first and second sensors; and
a display coupled to the controller;
the controller generating an indication on the display in response to the first sensor and the second sensor to selectively indicate and differentiate between the first and second types of contaminant in the fluid.

15. The rotary wing aircraft of claim 14 wherein:
the controller generates a first indication when neither the first sensor nor the second sensor produces a signal;
the controller generates a second indication when the first sensor produces a signal and the second sensor does not produce a signal to indicate a presence of the first type of contaminant in the fluid;
the controller generates a third indication when the first sensor does not produce a signal and the second sensor produces a signal to indicate a presence of the second type of contaminant in the fluid, the second type of contaminant being other than the first type and not being detectable by the first detector; and the controller generates a fourth indication when the first and second sensors both produce a signal to indicate a presence of a first type of contaminant in the lubricant and/or the presence of a second type of contaminant in the lubricant and in sufficient quantity to clog the inlet housing or detector screen.

16. The rotary wing aircraft of claim 12, wherein the first type is a metal contaminant and the second type is a non-metal contaminant.

17. The rotary wing aircraft of claim 12, wherein the second type of contaminant is not detectable by the first sensor.

* * * * *